United States Patent [19]

Tominaga et al.

[11] Patent Number: 4,543,827
[45] Date of Patent: Oct. 1, 1985

[54] METHOD FOR MEASURING PHYSICAL PROPERTIES OF MATERIAL

[75] Inventors: Ichiro Tominaga; Teruo Sasaki, both of Kobe, Japan

[73] Assignee: Sumitomo Rubber Industries, Kobe, Japan

[21] Appl. No.: 513,082

[22] Filed: Jul. 12, 1983

[30] Foreign Application Priority Data

Jul. 12, 1982 [JP] Japan .................. 57-121757
Jul. 12, 1982 [JP] Japan .................. 57-121758

[51] Int. Cl.⁴ .................. G01N 29/00; G01N 3/40
[52] U.S. Cl. .................. 73/602; 364/508; 364/487; 364/570; 73/573; 73/599
[58] Field of Search .......... 73/602, 573, 596, 598, 73/599, 597; 364/508, 560, 570, 487

[56] References Cited

U.S. PATENT DOCUMENTS

| | | | |
|---|---|---|---|
| 2,536,025 | 1/1951 | Blackburn | 73/597 X |
| 3,416,365 | 12/1968 | Frederick | 73/597 |
| 3,744,301 | 7/1973 | Aroue | 73/599 X |
| 3,771,355 | 11/1973 | Sachs | 73/597 |
| 4,065,665 | 12/1977 | Rietsch | 364/487 |
| 4,068,165 | 1/1978 | Labinsky et al. | 364/487 X |
| 4,192,003 | 3/1980 | Brock et al. | 364/487 |
| 4,231,094 | 10/1980 | Deblasche | 364/487 X |
| 4,275,446 | 6/1981 | Blaess | 364/487 |
| 4,289,032 | 9/1981 | Tominoga et al. | 73/599 |
| 4,338,948 | 7/1982 | Perez-Mendez et al. | 73/602 X |

FOREIGN PATENT DOCUMENTS

| | | | |
|---|---|---|---|
| 2037429 | 7/1980 | United Kingdom | 73/573 |
| 735960 | 5/1980 | U.S.S.R. | 73/573 |

*Primary Examiner*—Jerry W. Myracle
*Assistant Examiner*—Tom Noland
*Attorney, Agent, or Firm*—Birch, Stewart, Kolasch & Birch

[57] ABSTRACT

A method for measuring the physical properties of material comprising the steps of producing a tone burst wave by a tone burst wave oscillator, radiating acoustic energy of the tone burst wave onto an object to be measured to cause vibrations therein, detecting the vibrations as a waveform of an alternating wave at a vibration receiver, obtaining a gradient of a line which connects peaks in a first transitional region of the waveform from which can be determined the physical properties, in particular the energy transfer characteristics and/or restitution coefficient of the object.

4 Claims, 6 Drawing Figures

METHOD FOR MEASURING PHYSICAL PROPERTIES OF MATERIAL

BACKGROUND AND SUMMARY OF THE INVENTION

The present invention relates to a method for measuring the physical properties of a material.

The method according to the invention is particularly advantageous in measurement of the energy transfer characteristic and/or rebounding characteristic of an object.

More specifically, the method according to the invention can be advantageously utilized to determine the restitution coefficient of golf balls and the like.

In measurement of the energy transfer characteristic inherent to a material, a conventional method is known in which a viscoelasticity spectrometer is utilized to determine the energy transfer characteristic from energy loss caused by phase lag occurred when mechanical impulsive forces are applied to an object. However, this conventional method is accompanied by such a disadvantage that undesirable resonance will occur to hinder the exact measurement when more than 100 Hz of impulse frequencies are imparted to the object to be measured, and thus, an available upper limit of impulse frequencies usually remains at less than 100 Hz. In a particular case where more than 100 Hz is applied, a considerably expensive extra apparatus must be prepared to meet the requirement.

In measuring the physical properties of an object, several methods have heretofore been utilized in order to measure the rebounding characteristic or restitution coefficient of objects, such as golf balls. The simplest of these known methods is of man's actual performance of striking a ball. However, this method is naturally not too reliable in obtaining data because they depend on an individual's striking ability. Thus, another method which utilizes a striking machine in place of man's striking performance has been proposed, which is, however, disadvantageous in that the whole measuring system is quite expensive and not generally applicable.

Additionally, both of these known methods have another disadvantage in that various time consuming preliminary arrangements are required for effecting the measurng performance and obtaining data.

A further conventional method for measuring the restitution coefficient of golf balls is known in which a predetermined mass of projectile is shot against a sample golf ball by means of an air gun. However, this method also has a disadvantage that not only a large and expensive measuring system is inevitably required but also time consuming analysis are required before determining the restitution coefficient from the measured data.

As a matter of course, none of the above-discussed conventional methods are easily applicable to inspection of all of the products (golf balls) on the production line. In other words, the conventional methods are merely applicable to sampling inspection, from which, however, satisfactory inspection cannot be expected.

SUMMARY OF THE INVENTION

Differing from any of the above discussed conventional methods, the present invention is based on a principle that, in case a material has a good energy transfer characteristic, heat energy loss is small and that such a material as having a good energy transfer characteristic can be made to vibrate easily. The invention is also based on a principle that the energy transfer characteristic and restitution coefficient of a material are closely correlated with each other.

It is, therefore, an object of the present invention to provide a novel method for measuring the physical properties of an object, by which the above discussed disadvantages inherent to the prior art methods can be eliminated.

Another object of the invention is to provide a novel method for measuring the energy transfer characteristic of an object in a simple and economical manner without consuming too much time.

A further object of the invention is to provide a novel method for measuring the rebounding characteristic or restitution coefficient of an object, which is advantageous when utilized for the inspection of every product on a production line.

A still further object of the invention is to provide a novel method for determining the restitution coefficient of golf balls, in which the obtained data is quite reliable.

Other objects, features and advantages of the present invention will become apparent from the detailed description given hereinafter in connection with the accompanying drawings.

According to the present invention, there is provided a method for measuring the physical properties of a material, in particular the energy transfer characteristic and restitution coefficient of an object, which comprises the steps of producing a tone burst wave by a tone burst wave oscillator, radiating the acoustic energy of the tone burst wave onto the object to be measured to cause vibrations therein, detecting the vibrations as a waveform of an alternating wave at a vibration receiver, obtaining a gradient of a line which connects peaks in a first rising transitional region of the wave form, the gradient being capable of being analyzed to determine the energy transfer characteristic of the object.

According to the present invention, it is also possible to obtain the restitution coefficient of the material. For this purpose, the method further comprises additional steps of calculating a numerical value from the gradient, and multiplying the numerical value by a certain constant.

BRIEF DESCRIPTION OF THE DRAWINGS

In the accompanying drawings.

DESCRIPTION OF THE PREFERRED EMBODIMENTS

Figure 1:
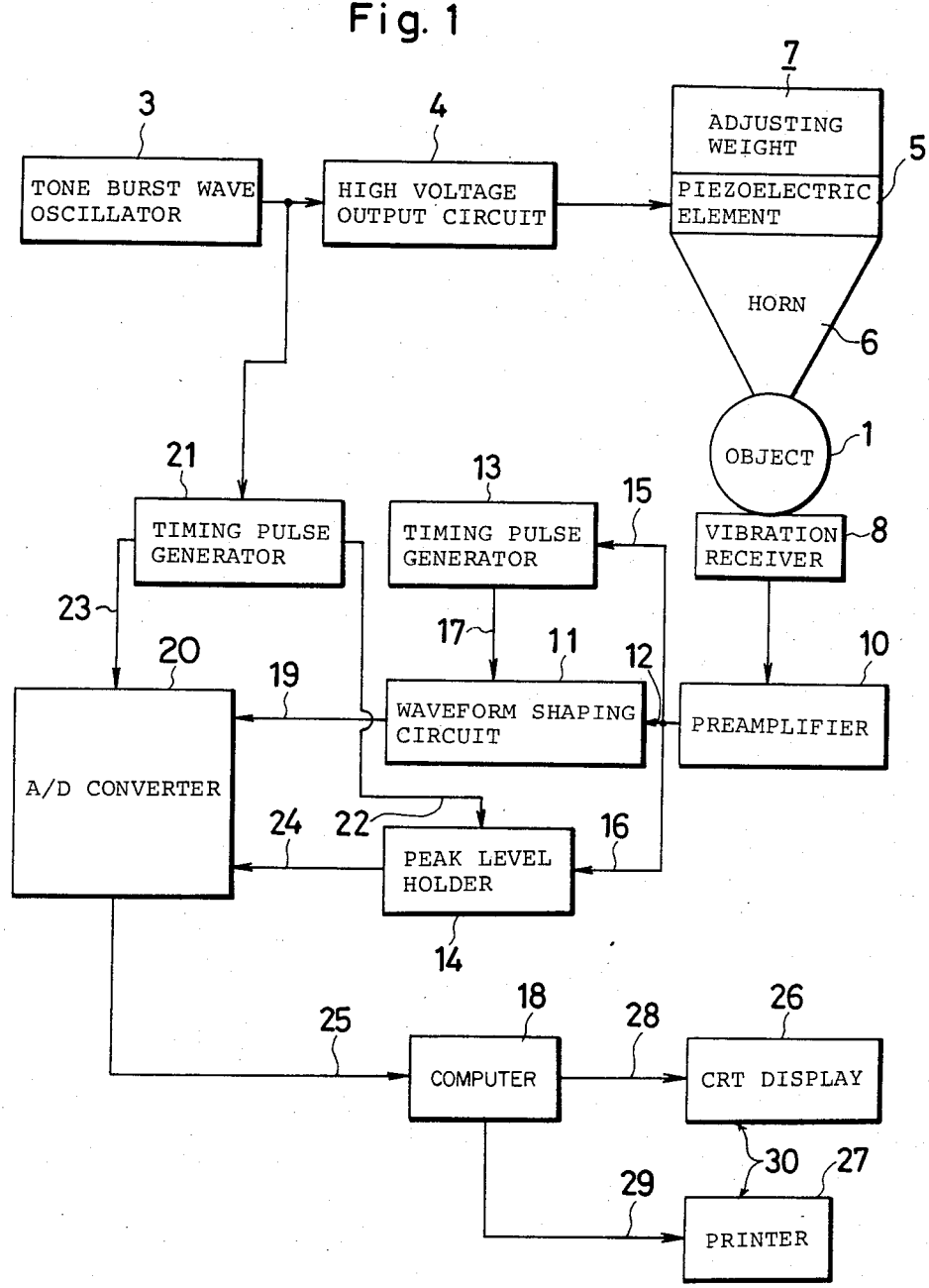
FIG. 1 is a block diagram showing one example of the method for measuring the energy transfer characteristic of an object, according to the present invention.

Referring now to the accompanying drawings, particularly to FIGS. 1 to 4, there is illustrated an object 1 to be measured for property identification. The object 1 may preferably be spherical or substantially spherical in configuration, as illustrated in FIG. 1, but it may be cubic or of any other configuration.

Figure 2:
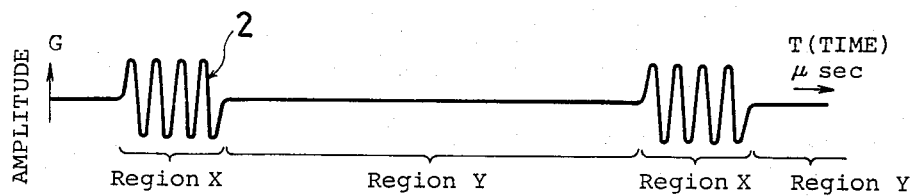
FIG. 2 is a diagram showing an example of a waveform of a tone burst wave.

According to the present invention, a tone burst wave 2 is used as a fundamental wave for checking energy transfer characteristic of the object 1. The tone burst wave is used within the range of the audio frequency band. More particularly, the tone burst wave can be shown in a coordinate system of time T (μsec), as the abscissa axis and amplitude G as the ordinate, axis as illustrated in FIG. 2, and for example, such a tone burst wave as having a waveform of repetition of the 4 to 8 cycle range (region X in FIG. 2) in oscillation and 20 to 40 cycle range (region Y in FIG. 2) in pause is suitable for use in carrying out the method of the present invention.

The tone burst wave 2 may be produced by a known tone burst wave oscillator 3, which is connected to a piezoelectric element 5 via a high voltage output circuit 4 which amplifies the output from the oscillator 3 to provide sufficiently high voltage and required current, so that the piezoelectric element is forcibly operated.

A horn 6, preferably a ultrasonic vibrating horn, which concentrates acoustic energy to its reduced forward end (lower end in illustration), is interposed between the piezoelectric element 5 and the object 1 to be measured. The horn 6 is in contact at its reduced end with a part of the object 1, in order that the concentrated acoustic energy is radiated onto the object 1. The horn 6 may preferably be made of plastic from the viewpoint of easy manufacturing, but it may be made of metal. The configuration of the horn 6 may be suitably selected in accordance with frequency and load.

A suitable adjusting weight 7 may be utilized for depressing the piezoelectric element 5 together with the horn 6, so that the forward end of the horn can maintain good contact relation with the object 1. The load of the weight 7 may be selected in accordance with hardness and other properties of the object 1.

A vibration receiver 8, which detects vibrations of the object 1 is an alternating wave 9 (FIG. 3), is in contact with a part of the object 1 in such a manner that the object 1 is sandwiched between the receiver 8 and the horn 6.

The alternating wave 9 (sound wave) detected by the vibration receiver 8 is amplified by a preamplifier 10, and the amplified output therefrom is inputted through connection 12 into a waveform shaping circuit 11.

At the same time, the output from the preamplifier 10 is separately inputted through connections 15, and 16 into a timing pulse generator 13 and a peak level holder 14. Timing signals from the timing pulse generator 13 are inputted into the waveform shaping circuit 11, which is required for data processing by a computer 18, as will be described hereinbelow.

Figure 3:
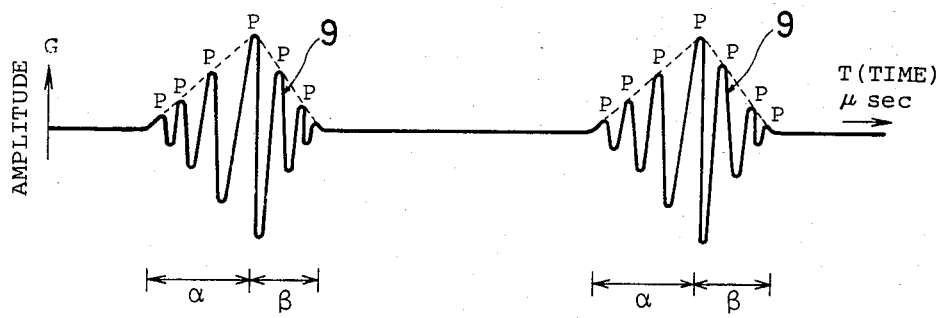
FIG. 3 is a view similar to FIG. 2, showing an example of a waveform of an alternating wave detected at a vibration receiver.
Figure 4:
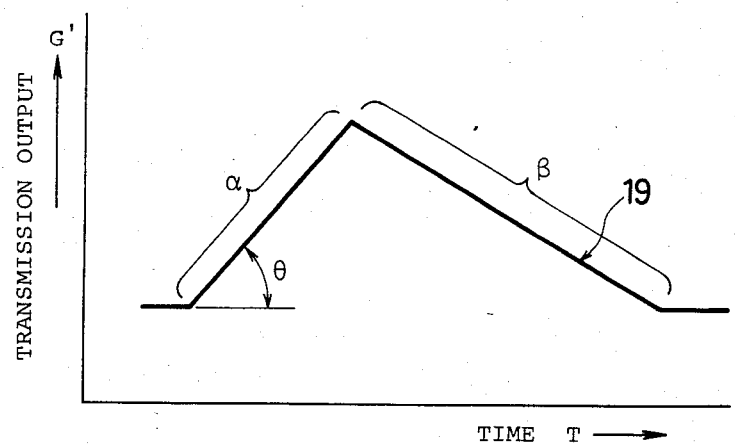
FIG. 4 is a graph or diagram showing an example of a linear image appearing on a CRT display.

Usually, for the purpose of data processing by the computer, A/D conversion is conducted at a sampling period of 50 to 100 μsec. However, in the case where a tone burst wave 2 of 5 KHz, for example, is used, the alternating wave 9 is oscillated at a period of approximately 200 μsec. Therefore, if the sampling period is 50 to 100 μsec., it is impossible to detect time-to-time variations in the wave amplitude G. Thus, it is necessary to provide the waveform shaping circuit 11 in order to regenerate peaks P of the alternating wave input 12 in accordance with the timing signals 17 from the timing pulse generator 13. In this way, direct current output 19, which corresponds to the amplitude G of the alternating wave 9, is inputted into an A/D converter 20, as shown in FIGS. 3 and 4.

A further timing pulse generator 21 is provided for receiving input signals from the tone burst wave oscillator 3 and separately transmitting the output pulses 22, and 23 therefrom to the peak level holder 14 and the A/D converter 20.

When the data obtained is processed by the computer, the peak level holder 14 maintains its output 24 at such a level as corresponding to a maximum value of a waveform used for standardization of the data, and inputs the output data 24 into the A/D converter 20. Incidentally, the maximum value of the waveform can also be calculated from the output 19 of the waveform shaping circuit 11. However, calculation from the peak level output 24 (FIG. 1) is more advantageous because it permits reduction of calculation time by the computer 18 since calculation for data-processing can be simplified.

Both the direct current output 19 from the waveform shaping circuit 11 and the output 24 from the peak level holder 14 are put into A/D conversion at the A/D converter 20 by the pulses 23, and the output data 25 from the A/D converter 20 are processed by the computer 18. The processed data from the computer 18 are outputted through connections 28, and 29 into suitable display devices, respectively. In the illustrated embodiments, a CRT display 26 and a printer 27 are utilized as the display devices. It is also possible to utilize other display devices instead of the CRT display and the printer.

One example of the linear image appearing on the CRT display is shown in FIG. 4, with time T as a horizontal axis and transmitted output G as a vertical axis. In FIG. 4, reference character α designates a first transitional or rising region in which vibration amplitude in the object 1 is gradually increased by acoustic energy applied thereto, while reference character β designates an aftershock region wherein excitation to the object is ceased and the vibration amplitude in the object 1 is gradually attenuated. The energy transfer characteristic of the object 1 can be determined by a value of gradient (tan θ) of the first transitional region α.

If the object 1 has a good energy transfer characteristic, heat energy loss is small at the time when the tone burst wave 2 is radiated upon the object 1 to cause vibrations therein. The object having a good energy transfer characteristic can be made to vibrate easily, resulting in a large gradient (tan θ) in FIG. 4.

In contrast thereto, if the object 1 has a poor energy transfer characteristic, the gradient of the first transitional region α is small. In this manner, the energy transfer characteristic of the object 1 can be determined by the gradient (tan θ) of the first transitional region α.

Figure 5:
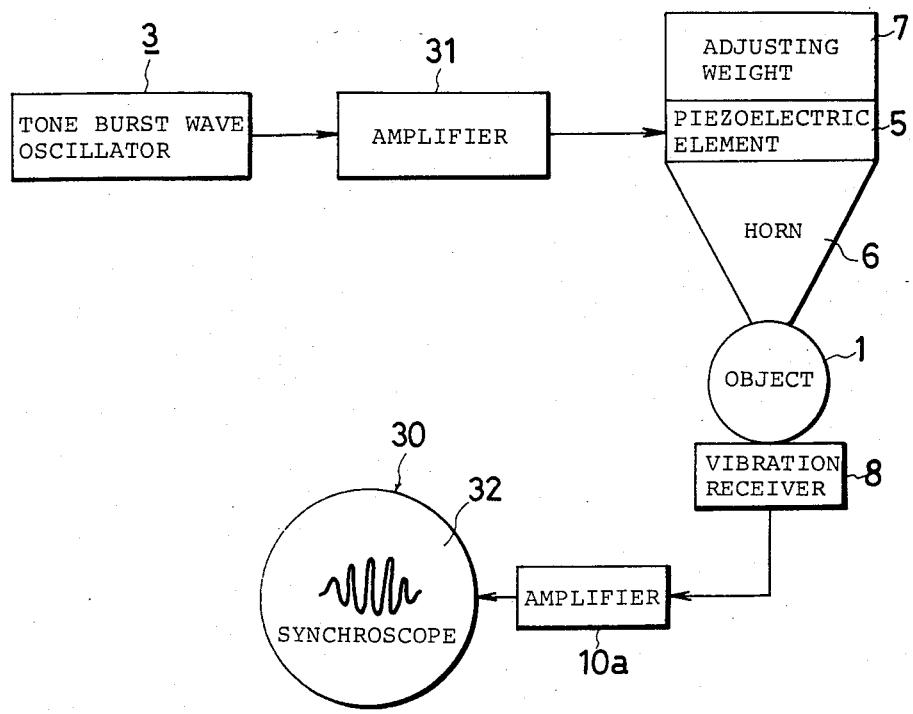
FIG. 5 is a block diagram showing the method for measuring the rebounding characteristic of an object, according to the invention.

FIG. 5 illustrates an example of simplified process of the method, which also can be utilized for measuring restitution coefficient of an object, for example a golf ball or the like, wherein a tone burst wave oscillator 3 is used to produce repetition of oscillation (region X) and pause (region Y) as shown in FIG. 2.

In the case where the object 1 to be measured is a ball such as a golf ball, frequencies in the range of 600 Hz to 20 KHz are preferable to use. The output from the tone burst wave oscillator 3 is amplified at an amplifier 31 and then inputted into a piezoelectric element 5 for operating the same. The object 1 is in contact with a ultrasonic vibrating horn 6 for receiving acoustic energy from its reduced end.

An accelerometer may be used as a vibration receiver 8, and the output therefrom is amplified by an amplifier 10a. As a display device 30 for displaying the waveforms detected at the vibration receiver 8, a synchroscope 32 may preferably be utilized.

The waveform of the exciting tone burst wave 2 is substantially the same as that shown in FIG. 2 of which full description has been made in detail above, while the waveform displayed on the synchroscope 32 is substantially the same as that shown in FIG. 3.

Figure 6:
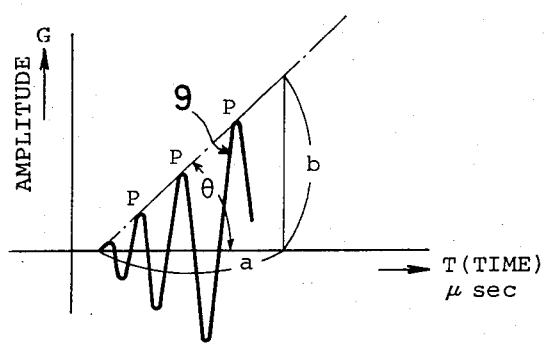
FIG. 6 is a diagram showing another example of a waveform of a first transition or rising region of the alternating wave detected at the vibration receiver.

As is apparent from FIGS. 2, 3 and 6, when the object 1 is made to vibrate by the tone burst wave 2 of a constant amplitude, the waveform of the alternating wave 9 detected at the side of the vibration receiver 8 is gradually increased in amplitude to its maximum, and this first transition or initial rising region, that is, a range of forcible vibration, is shown and designated in FIG. 3 by reference character α. Upon ceasing the excitation, the wave 9 decreases in amplitude and this second transition, that is, aftershock region, is designated by reference character α in FIG. 3.

The reason why a difference in magnitude of restitution coefficient arises is considered as follows:

For example, when striking energy is imparted to a golf ball by a golf club, a part of the imparted energy is converted to heat energy and consumed internally by the golf ball. It has been proved by repeated experiments that restitution coefficient of golf balls is larger with a smaller consumption rate of the heat energy, while smaller with a larger consumption rate of the heat energy. When considering this from the viewpoint of vibration, it is considered that vibration frequencies generated by striking a golf ball range approximately from 800 Hz to 10 KHz at most, judging from an average contact time of a golf ball with a golf club. If other balls, such as those for a baseball game or the like are included herein, the vibration frequencies may range from 600 Hz to 20 KHz. Accordingly, it is assumed that such energy loss (consumed as heat energy in a ball) as observed when vibration of 600 Hz to 20 KHz, more particularly of 800 Hz to 10 KHz, is applied to a ball, has a certain relation to the restitution coefficient of the ball.

When analysing the various waveforms appearing on the synchroscope 5 (FIG. 5) with respect to various golf balls having different restitution coefficients, it is observed that the amplitude G of the rising region α increases rapidly when the energy loss is small as shown in FIGS. 3 and 6. In contrast thereto, when the energy loss is large, the amplitude in the region α increases relatively gradually. When peaks P of the wave 9 are connected with a straight line as shown in FIGS. 3 and 6, it may be said that a value of gradient (tan θ) of the straight line shows a degree of the energy loss. In other words, a degree of ease to forcibly vibrate a golf ball is numerically presented.

In order to prove the above, an experiment was carried out under the following conditions:

A SEI piezoelectric ceramic oscillator (ELCON) was used as a tone burst wave oscillator 3. A tone burst wave of 4.8 KHz frequency was produced by the oscillator 3. The waveform of the tone burst wave thus produced was of repetition of 4 cycle range in oscillation and 12 cycle range in pause (FIG. 2). A PMMA-made horn 6 with a resonant frequency of 4.8 KHz was employed, whose dimension was 150 mm in axial length, 8 mm in reduced forward end diameter, and 26 mm in rear end diameter. An accelerometer was employed as the vibration receiver 8. A gradient (tan θ) was determined by obtaining a ratio of b/a as shown in FIG. 6.

On the other hand, the following experiment was carried out for the purpose of comparison and determination of restitution coefficient of a golf ball.

According to the conventional method, an aluminium projectile of 200 g mass was shot from a known air gun at a speed of 40 m/sec to hit a standstill golf ball. Then, after measuring an initial speed of the golf ball just after it is hit by a projectile (environmental temperature 25° C.) i.e. the speed of the ball immediately after impact, the restitution coefficient of the golf ball was sought by the following equation:

$$e = Vb/VH \, (1 + m/M) - 1$$

where,
e: restitution coefficient
m: mass of golf ball (g)
M: mass of projectile (g)
VH: speed of projectile (m/sec)
Vb: initial speed of golf ball (m/sec)

Measured values of the gradient and the restitution coefficient obtained through the above two experiments are shown in the following table.

| Ball No. | Hardness of Ball | Restitution Coefficient | Gradient tan θ (V/μsec) |
| --- | --- | --- | --- |
| 1 | 74 | 0.730 | 8.3 |
| 2 | 78 | 0.734 | 8.5 |
| 3 | 78 | 0.728 | 7.7 |
| 4 | 78 | 0.730 | 9.6 |
| 5 | 78 | 0.736 | 8.3 |
| 6 | 78 | 0.713 | 3.6 |
| 7 | 76 | 0.709 | 3.5 |
| 8 | 77 | 0.719 | 3.9 |
| 9 | 78 | 0.711 | 3.9 |
| 10 | 78 | 0.708 | 4.2 |
| 11 | 86 | 0.724 | 7.0 |
| 12 | 90 | 0.726 | 10.0 |
| 13 | 90 | 0.734 | 11.1 |
| 14 | 90 | 0.728 | 9.6 |
| 15 | 88 | 0.719 | 7.8 |
| 16 | 84 | 0.722 | 7.0 |
| 17 | 86 | 0.718 | 6.9 |
| 18 | 86 | 0.723 | 7.0 |
| 19 | 86 | 0.725 | 7.2 |
| 20 | 86 | 0.721 | 6.8 |
| 21 | 86 | 0.720 | 7.0 |
| 22 | 82 | 0.724 | 7.5 |
| 23 | 82 | 0.723 | 7.0 |
| 24 | 82 | 0.718 | 6.5 |
| 25 | 82 | 0.719 | 6.8 |
| 26 | 74 | 0.707 | 4.5 |
| 27 | 74 | 0.710 | 4.4 |
| 28 | 78 | 0.716 | 4.5 |
| 29 | 78 | 0.714 | 5.0 |
| 30 | 74 | 0.708 | 4.3 |
| 31 | 74 | 0.707 | 4.6 |
| 32 | 82 | 0.746 | 10.8 |
| 33 | 83 | 0.745 | 11.9 |
| 34 | 82 | 0.747 | 11.5 |
| 35 | 84 | 0.739 | 11.3 |
| 36 | 72 | 0.707 | 3.9 |

By comparing the measured values of the restitution coefficient (e) with the measured values of the gradient (tan θ), a value of the coefficient of correlation therebetween has proved to be 0.924. Consequently, it is clear that a close correlation exists between the numerical values relating to the ease to forcibly vibrate an object to be measured, that is, the gradient (tan θ), and the numerical values of the restitution coefficient (e) determined in accordance with the conventional method.

By employing the tone burst wave of 600 Hz to 20 KHz, preferably 800 Hz to 10 KHz, in vibration frequency, the vibration frequency of the golf ball, which can be calculated from the contact time when the ball is hit by the golf club, is surely included within the above frequency range of the tone burst wave, and the aforedescribed energy loss as heat energy consumption in the golf ball caused by forced vibrations by the tone burst wave is closely correlated with the energy loss as heat energy consumption in the golf ball caused when it was hit by the golf club.

Further, by employing the tone burst wave, each of the initial rising regions α as well as each of the aftershock regions β can be clearly (FIGS. 3 and 6) at each time when the golf ball is forcily vibrated.

As will be easily understood from the foregoing description, the method of the present invention are applicable to various objects different in material, shape, dimension and/or utility.

For the purpose of measuring restitution coefficient of an object, either of the processes shown in FIGS. 1 and 5 may be utilized to obtain the required gradient (tan θ) of the rising region α as described hereinbefore.

According to the present invention, the desired measurement of the energy transfer characteristic is carried out by analysing the gradient (tan θ) of the rising portion α in the alternating wave 9 as described, and therefore, the method can be applied to such a high frequency range as exceeding 100 Hz without invinting a problem of resonance.

The present invention being thus described, it will be obvious that same may be varied in many ways. Such variations are not to be regarded as a departure from the spirit and scope of the invention, and all such modifications as would be obvious to one skilled in the art are intended to be included within the scope.

We claim:

1. A method for measuring physical properties of material which comprises the steps of
   producing a tone burst wave by a tone burst wave oscillator,
   radiating acoustic energy of said tone burst wave onto an object to be measured to cause vibrations therein,
   detecting said vibrations as a waveform of an alternating wave at a vibration receiver, and
   obtaining a gradient of a line which connects peaks in a first transitional region of said waveform corresponding to a first region where an amplitude of successive waves in the received waveforms is increasing to determine energy transfer characteristic of said object which is a ratio of a quantity of output energy to a quantity of input energy.

2. The method as defined in claim 1, which further comprises
   regenerating said peaks of said alternating wave by a waveform shaping circuit to produce a direct current output corresponding to respective amplitudes of said peaks of said alternating wave;
   conducting A/D conversion of said direct current output to obtain output data therefrom;
   introducing said output data to a computer for processing and directing said processed data to a display device to determine said energy transfer characteristic of said object.

3. The method as defined in claim 1, which further comprises
   calculating a numerical value from said gradient, and
   multiplying said numerical value by a constant to obtain a restitution coefficient of said object.

4. The method as defined in claim 1, wherein
   said tone burst wave ranges from 600 Hz to 20 Hz in frequency, and
   said object to be measured is a golf ball.

* * * * *